United States Patent
Colvin et al.

(10) Patent No.: US 11,053,326 B2
(45) Date of Patent: Jul. 6, 2021

(54) OXIDATION RESISTANT NATURAL RUBBER AND A METHOD FOR ITS PRODUCTION

(71) Applicant: COOPER TIRE & RUBBER COMPANY, Findlay, OH (US)

(72) Inventors: Howard A. Colvin, Wayne, OH (US); Zachary D. Walters, Findlay, OH (US)

(73) Assignee: Cooper Tire and Rubber Company, Findlay, OH (US)

( * ) Notice: Subject to any disclaimer, the term of this patent is extended or adjusted under 35 U.S.C. 154(b) by 0 days.

(21) Appl. No.: 15/509,630

(22) PCT Filed: Sep. 10, 2015

(86) PCT No.: PCT/US2015/049469
§ 371 (c)(1),
(2) Date: Mar. 8, 2017

(87) PCT Pub. No.: WO2016/040665
PCT Pub. Date: Mar. 17, 2016

(65) Prior Publication Data
US 2017/0247477 A1    Aug. 31, 2017

Related U.S. Application Data

(60) Provisional application No. 62/049,943, filed on Sep. 12, 2014.

(51) Int. Cl.
| | |
|---|---|
| *C08C 19/22* | (2006.01) |
| *C08K 5/00* | (2006.01) |
| *B60C 1/00* | (2006.01) |
| *C08C 1/02* | (2006.01) |
| *C08K 5/18* | (2006.01) |
| *C08K 5/375* | (2006.01) |
| *C08F 136/08* | (2006.01) |
| *C08C 19/20* | (2006.01) |
| *C08L 7/02* | (2006.01) |
| *C08C 1/14* | (2006.01) |
| *C12N 9/88* | (2006.01) |

(52) U.S. Cl.
CPC ............... *C08C 19/22* (2013.01); *B60C 1/00* (2013.01); *C08C 1/02* (2013.01); *C08C 1/14* (2013.01); *C08C 19/20* (2013.01); *C08F 136/08* (2013.01); *C08K 5/005* (2013.01); *C08K 5/18* (2013.01); *C08K 5/375* (2013.01); *C08L 7/02* (2013.01); *C12N 9/88* (2013.01); *C12Y 402/01092* (2013.01)

(58) Field of Classification Search
CPC .. C08C 19/22; C08C 1/02; C08C 1/14; C08C 19/20; C08K 5/18; C08K 5/375; C08K 5/005; C08L 7/02; C12N 9/88; C12Y 402/010902; B60C 1/00; C08F 136/08
See application file for complete search history.

(56) References Cited

U.S. PATENT DOCUMENTS

| | | | | |
|---|---|---|---|---|
| 4,435,337 A | * | 3/1984 | Kay | .............. C08J 11/06 528/491 |
| 4,526,959 A | | 7/1985 | Kay | |
| 5,998,512 A | * | 12/1999 | Schloman | .............. C08C 1/04 524/17 |
| 2011/0054051 A1 | | 3/2011 | Cole | |

FOREIGN PATENT DOCUMENTS

WO    2014-047176 A1    3/2014

OTHER PUBLICATIONS

Katbab, et al., Mechanisms of antioxidant action: The behaviour of a bound antioxidant as an antiozonant, Polymer Degradation and Stability, 1981, vol. 3, No. 3, pp. 221-227.
Schloman, Jr., Processing guayule for latex and bulk rubber, Industrial Crops and Products, 2005, vol. 22, No. 1, pp. 41-47.
E. Ceausescu et al., "Diene rubber modification using thiol-type dertivatives", CA, Dec. 31, 1985, XP002225947, Abstract.
G. Scott et al., "Mechanisms of antioxidant: Technological effectiveness of sulphur based bound antioxidants in NR and SBR", Polymer Degradation and Stability, Barking GB, vol. 4, No. 4, Jul. 1, 1982, pp. 267-278, XP024143515, ISSN: 0141-3910, *p. 277; tables 2-3*.
G. Scott: "Wege Zur Herstellung Alterungsbestaendiger Gummisorten", Gummi, Fasern, Kunststoffe: Fachmagazin Fuer Die Polymerindustrie, vol. 36, Jan. 1, 1993, pp. 276-278, XP055461611, DE, ISSN: 0017-5595, *p. 278, col. 2-col. 3*.

* cited by examiner

*Primary Examiner* — Patrick D Niland
(74) *Attorney, Agent, or Firm* — Fay Sharpe LLP

(57) ABSTRACT

A method for stabilizing a natural rubber such as guayule. The method includes the step of introducing at least one of an Extraction Curves for Guayule Rubber Samples amine and a phenolic anti-oxidant, such as MADA, to a latex form of the rubber under conditions such that the anti-oxidant becomes chemically bound to the rubber. The method includes the further step of subsequently treating the rubber to remove at least a substantial portion of entrained resins. The method can yield a rubber composition of, for example, guayule rubber and including an anti-oxidant chemically bound thereto. The resultant rubber can be suitable for use in tire construction.

17 Claims, 4 Drawing Sheets

OXIDATION RESISTANT NATURAL RUBBER AND A METHOD FOR ITS PRODUCTION

BACKGROUND

The present exemplary embodiment relates to a method for producing an oxidation resistant natural rubber, and the rubber produced thereby. It finds particular application in conjunction with guayule rubber, and will be described with reference thereto. However, it is to be appreciated that the present exemplary embodiment is also amenable to other similar applications.

Natural rubber, derived from the plant *Hevea brasiliensis*, is a core component of many consumer goods, including medical devices and products, such as latex gloves. The United States has a strong reliance on natural rubber, primarily because synthetic alternatives cannot match the high performance properties of natural rubber required for many applications and tend to be prohibitively expensive.

Over 90% of the *Hevea*-derived natural rubber imported by the United States originates in Indonesia, Malaysia and Thailand. Natural rubber sources in these countries are under intense threat from potential diseases and blights due to the genetic similarity of the rubber plants. Furthermore, the crop is limited by a restricted geographic area and labor-intensive harvesting methods. In addition, the Southeast Asian natural rubber crop contains many protein contaminants which are responsible for Type-I latex allergies, which are estimated to affect as many as 20 million Americans.

The high cost of importation to the United States, as well as the potential for the entire crop to be wiped out by disease and the ubiquity of latex allergies, make non-allergenic domestic natural rubber alternatives particularly attractive.

As an alternative to synthetic rubber sources, attention is being directed to the production of natural rubber in plants such as guayule (*Parthenium argentatum*), a desert plant native to the southwestern United States and northern Mexico. Guayule yields polymeric cis 1,4-isoprene essentially identical to that produced by *Hevea* rubber trees in Southeast Asia.

BRIEF DESCRIPTION

Various details of the present disclosure are hereinafter summarized to provide a basic understanding. This summary is not an extensive overview of the disclosure and is neither intended to identify certain elements of the disclosure, nor to delineate scope thereof. Rather, the primary purpose of this summary is to present some concepts of the disclosure in a simplified form prior to the more detailed description that is presented hereinafter.

According to a first embodiment, a method for stabilizing a natural rubber such as guayule is provided. The method includes the step of introducing 4-(mercapto acetamido) diphenylamine, hereinafter referred to as MADA, to a latex form of the rubber under conditions such that the MADA becomes chemically bound to the rubber. The method includes the further step of subsequently treating the rubber to remove a substantial portion of entrained resins.

According to a second embodiment, a method for stabilizing a natural rubber such as guayule is provided. The method includes the step of introducing at least one of an amine or a phenolic anti-oxidant to a latex form of the rubber under conditions such that the anti-oxidant becomes chemically bound to the rubber. The method includes the further step of subsequently treating the rubber to remove at least a substantial portion of entrained resins.

According to a further embodiment, a rubber composition comprised of cis-1,4-polyisoprene and including an anti-oxidant chemically bound thereto is provided. The composition contains less than 20% of the proteins associated with *Hevea* rubber and further includes at least a trace of resins present in other natural rubbers. The rubber may also include an allene oxide synthase protein such as 53-KDa monoxygenase P450. Although it is believed that a significant amount of the allene oxide synthase protein will be present in a post extraction rubber, the present disclosure also contemplates that a portion may be removed during the resin extraction process.

According to an additional embodiment, a rubber composition comprised of guayule rubber and including an anti-oxidant chemically bound thereto is provided. The composition further includes between at least a trace and 4%, preferably between a trace and 3%, of resins present in guayule rubbers.

According to another embodiment, a tire including the rubber composition of cis-1,4-polyisoprene and including an anti-oxidant chemically bound thereto is provided. The composition contains less than 20% of the proteins associated with Hevea rubber and further includes at least a trace of resins present in other natural rubbers. The rubber may also include an allene oxide synthase protein such as 53-KDa monoxygenase P450. Although it is believed that a significant amount of the allene oxide synthase protein will be present in a post extraction rubber, the present disclosure also contemplates that a portion may be removed during the resin extraction process. According to another embodiment, a tire including the rubber composition of guayule rubber and including an anti-oxidant chemically bound thereto is provided. The composition further includes between at least a trace and 4%, preferably between a trace and 3%, of resins present in guayule rubbers.

DETAILED DESCRIPTION

Figure 1:
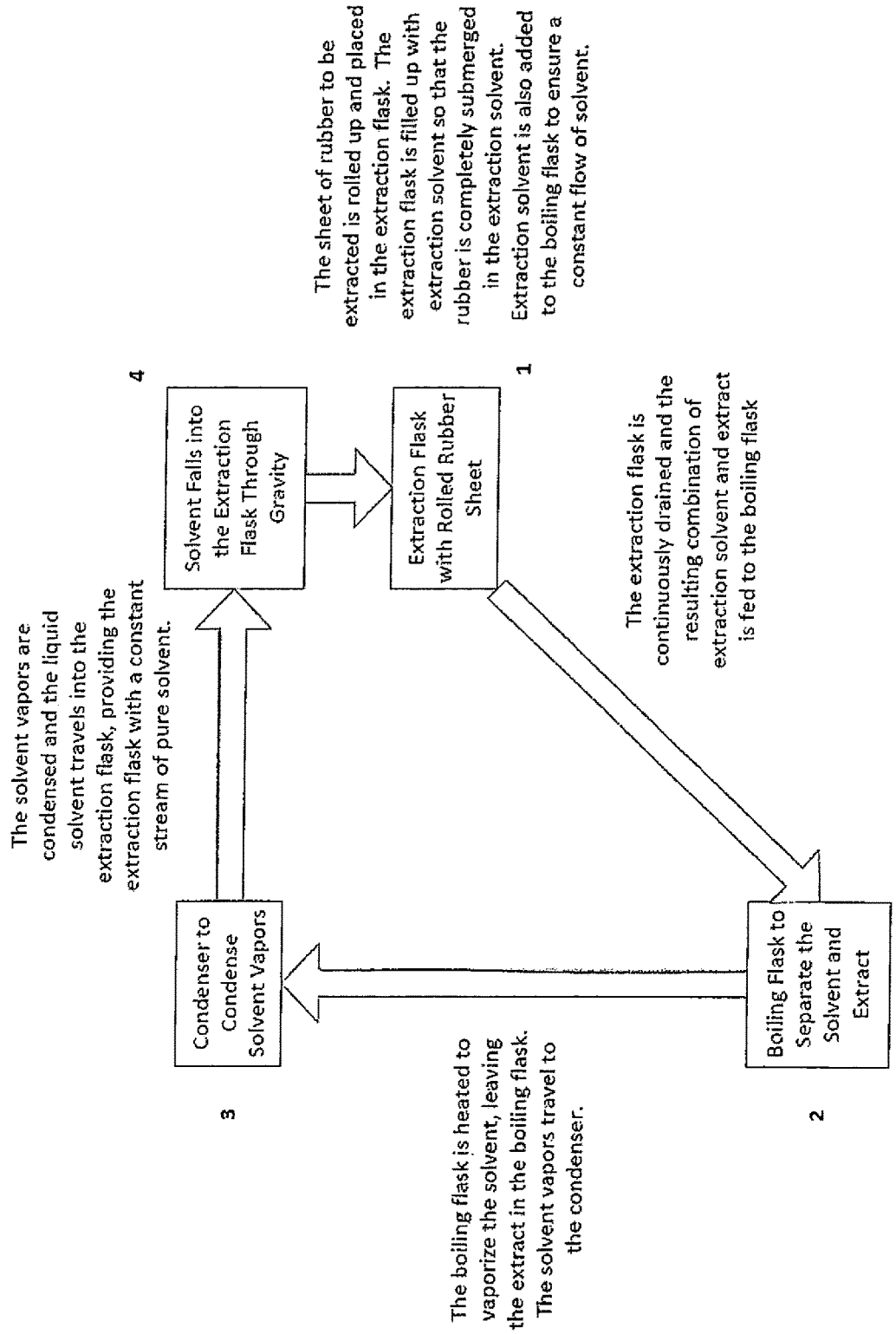
FIG. 1 schematically illustrates a continuous extraction process for guayule

The processing of native desert plants for the extraction of biopolymers such as natural rubber latex can be achieved using chemical and/or mechanical processing. The methods utilized typically follow the general steps of: pre-grinding, wet milling, filtration, clarification, separation of liquid phases, purification, creaming, and concentration. Exemplary harvesting/processing techniques are described in U.S. Pat. No. 7,923,039 and US Patent Publication 2008/0015336, the disclosures of which are herein incorporated by reference.

Non-limiting examples of plant materials that can be used include, but are not limited to, guayule plant (*Parthenium argentatum*), gopher plant (*Euphorbia lathyris*), mariola (*Parthenium incanum*), rabbitbrush (*Chrysothamnus nauseosus*), milkweeds (*Asclepias L.*), goldenrods (*Solidago*), pale Indian plantain (*Cacalia atripilcifolia*), rubber vine (*Crypstogeia grandiflora*), Russian dandelions (*Taraxacum kok-saghyz*), mountain mint (*Pycnanthemum incanum*), American germander (*Teucreum canadense*) and tall bellflower (*Campanula americana*).

The process disclosed herein extracts and purifies biopolymers such as natural rubber from non-*Hevea* plants. The extracted biopolymers may then be processed for a variety of commercial uses, for example, products such as tires and hoses.

Using guayule as an exemplary species, the plant is harvested by hedging or pollarding (cutting the trunk of the plant above the root base), so that only above-ground portions of the plant are harvested and subsequently processed. The plants may be defoliated using mechanized shearing, hand shearing, hedge shearing, or with non-dehydrating chemical defoliants. After harvest, the plants are sent to a chopper capable of chopping the plant pieces into a relatively uniform size or shape. The latex rubber is located near the bark of the chopped guayule sticks and root components. The chopper chops the plants into uniform pieces to enable a separator system to remove a major portion of the leaves, flowers, and small stems and then prepare the larger stems for de-barking and wet milling operations for latex rubber extraction. Larger pieces (e.g., bark, chopped plant, and pulp) are discharged from the separator and conveyed to a further processing step.

Following separation, plants can be chemically treated. The chemical treatment can comprise the addition of a water-based solution to emulsify the plant material to form a slurry during a milling step, followed by a first press step, and a washing step. The chemical treatment will yield a solid product containing a biomass by-product called "bagasse" and liquid homogenate slurry containing water-based solution and dilute latex from milled plant material.

The chemical treatment can optionally add anti-microbial agents, de-foaming or anti-foaming agents, bleaching agents, and/or stabilizers depending on desired product quality, stability, color, purity or sterility requirements. Further, anti-oxidants, such as sodium sulfite, butylated hydroxytoluene (BHT), butylated hydroxyanisole (BHA), ascorbate, propyl gallate, alkylated diphenylamine, polybutylated bisphenol A, alkylated para-phenylenediamine, styrenated phenol, or hindered bisphenol may be added. However, as described within this disclosure, the addition of these types of anti-oxidants at this stage of the guayule processing has been found to be relatively ineffective when trying to isolate rubber from the latex for applications such as tires.

The next step in the process is pressing. Pressing removes a major portion of the latex rubber from the bagasse. Particularly, the latex rubber is suspended in an aqueous solution as an emulsion and is removed from the biomass emulsion slurry by squeezing the liquids from the slurry. The liquid phase, or latex homogenate liquid slurry, can be passed through a screen, while the solid bagasse does not pass through the screen. The liquid latex homogenate slurry can be collected in a tank and the bagasse moved to a separate collection area for use in secondary manufacturing processes such as for resin extraction, fuel, particle board, and ethanol production.

The latex-containing homogenate liquid is then fed to a series of separators to further remove fine solids from the emulsion and concentrate the latex rubber emulsion by removing water and aqueous waste.

The latex may then be subjected to a creaming treatment. The creaming system allows the latex rubber emulsion to partially coagulate until it reaches the desired concentration (e.g., 50-60 wt % latex rubber concentration in water), and also removes many undesirable proteins and impurities. The creaming mix tank can be an agitated vessel with heating and cooling to control the temperature and can contain a solution comprised of a coagulant, stabilizers, and an antioxidant. The upper layer containing a latex rubber phase is transferred to a latex product tank, for testing and then ultimately transferred for product storage.

Commercially produced guayule latex processed as described above contains levels of resin (low-molecular weight, acetone-extractable material) that, when coagulated, can make the rubber unsuitable for certain applications such as tires. Unlike *Hevea*, guayule does not produce latex in a specialized system of lacticifers. Instead, latex is formed and stored in individual cells. Therefore, the coagulation process introduces both rubber and non-rubber components into the rubber. In this regard, isolated guayule rubber can contain in excess of 20% by weight resin. Resin is an undesirable constituent because it acts as a plasticizer and will adversely affect the cure rate and cure state of compounds. Thus, it is desirable to remove the resins from the coagulated rubber by extraction with solvents or a mixture of solvents. Examples of such extraction media include acetone, an acetone-pentane azeotrope, or alcohols containing four or fewer carbon atoms. One problem with the extraction procedure typically used with guayule is that it is performed as a batch process—that is the guayule rubber is submerged in the extraction media for a lengthy period of time before the resin is extracted. In most cases multiple batch extractions are required to remove enough resin to give tire grade guayule.

As mentioned earlier, one major advantage of guayule rubber is that its does not cause allergic reactions in people who are subject to those reactions when exposed to *Hevea* rubber. This effect is due to the differences and relative amounts of proteins present in each species. *Hevea* rubber possesses many different types of proteins with a 14-kDa "rubber elongation factor" and a 24-kDa "small rubber particle protein" (SRPP) dominating. Both of these are known allergens. In guayule, there are few proteins. 53-kDa monoxygenase P450 (an allene oxide synthase) comprises about 50% of the rubber particle protein (see M. Whalen, C. McMahan and D. Shintani, "Development of Crops to Produce Industrially Useful Natural Rubber, Isoprenoid Synthesis in Plants and Microorganisms: New Concepts and Experimental Approaches, pages 329-345, T. Bach and M. Rohmer eds, 2013; the disclosure of which is herein incorporated by reference). Thus, although the chemical structure of the rubber in both species are similar (cis-1,4 polyisoprene), the overall composition of the rubbers is not identical.

Although the protein advantages of guayule are outlined above, the lack of proteins and other natural anti-oxidants make guayule more susceptible to degradation from oxygen and heat. Accordingly, as mentioned above, anti-oxidants are frequently introduced. For example, as disclosed in Processing Guayule for Latex and Bulk Rubber, Industrial Crops and Products 22 (2005) 41-47, herein incorporated by reference, it is suggested to add an anti-oxidant after initially milling the freshly harvested shrub in water. Once the shrub is processed to isolate the latex, and then the rubber, much of the antioxidant may be removed. Moreover, when the coagulated guayule rubber is extracted to remove resin, the antioxidant is also removed. Evidence of antioxidant removal during extraction can be inferred from a determination that incorporation of anti-oxidant into the acetone extraction media during a batch extraction does not provide a Mooney retention index value (MRI) of 0.85 which is desirable for tire grade rubber. Mooney retention index is characterized herein as a test where a rubber sample is tested for Mooney viscosity, then aged for 30 minutes at 290° F., and Mooney viscosity is measured on the aged sample. The Mooney viscosity value of the aged sample is divided by the original Mooney viscosity to give a ratio indicative of the Mooney retention. If the rubber does not contain sufficient antioxidant because of the extraction process, it is highly susceptible to oxidation and will typically require the undesirable and costly step of re-introducing an anti-oxidant. In fact, it has been found that even the physical step of introducing an anti-oxidant to the rubber after resin removal using conventional rubber mixing technology can cause some degradation.

Although guayule has been used in tires since the beginning of the 20$^{th}$ century, a viable commercialized process for producing tire grade rubber from latex is not believed to have been discovered. The present disclosure provides a process for the preparation of tire grade guayule rubber which involves the continuous extraction of a guayule rubber isolated from latex with a polar solvent such as acetone, where the guayule rubber latex has been reacted with an anti-oxidant in such a way that the anti-oxidant has been at least partially bound to the guayule. The present invention overcomes some of the shortcomings associated with guayule processing by 1) incorporation of an anti-oxidant, such as MADA (shown in Formula 1), into the rubber in a manner that largely prevents extraction of the anti-oxidant during resin removal and 2) removal of acetone extractables by use of a continuous extraction.

Formula 1

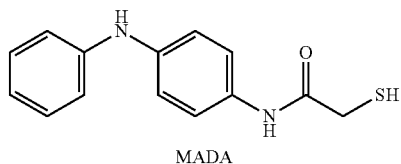

MADA

Typically, extractables are removed from guayule rubber by batch extraction. In this method, a sample of guayule rubber is placed into a container holding a polar solvent for a period of time followed by removal from the solvent and measurement of the extractables. The solvent is typically changed every 24 hours, and the guayule is extracted again to remove more extractables. This is a time consuming, but effective technique to remove extractables. As can be seen from Table 1 it can take more than 48 hours of extraction to bring the extractables to below 3-4% which is a target for guayule rubber in tire applications.

TABLE 1

Batch extraction of guayule rubber in acetone

| Time of extraction (hrs) | Extractables | % Extractables removed |
|---|---|---|
| 0 | 10.51 | 0.0 |
| 24 | 5.91 | 43.7 |
| 48 | 3.62 | 65.6 |
| 96 | 3.34 | 68.2 |
| 120 | 1.96 | 81.3 |

In one embodiment the continuous extraction of guayule employs a process as described in FIG. 1. In this embodiment, the guayule sees "fresh" solvent continuously and thus the extractables are removed faster. Removal of extractables using a continuous process is shown in Table 2. Comparison of the rates of extraction between Tables 1 and 2 clearly show the superiority of the continuous process over the batch process. This behavior is also seen with guayule containing MADA.

TABLE 2

Continuous extraction of guayule rubber in acetone

| Time of extraction (hrs) | Extractables | % Extractables removed |
|---|---|---|
| 0 | 21.57 | 0.0 |
| 8 | 6.47 | 70.0 |
| 16 | 3.62 | 83.2 |

As stated previously, guayule rubber contains "acetone extractables" that must be extracted out of the rubber in order to maintain properties similar to *Hevea* natural rubber. In certain embodiments, it is desirable for the extractable content in guayule rubber to be less than 4%, preferably less than 3%. However, when extracting the "acetone extractables" from the rubber, the antioxidant that has traditionally been added during guayule production is extracted as well. The present embodiment is directed to a process that stabilizes the guayule rubber before extraction and maintains the stabilization throughout the extraction and drying steps. The present embodiment employs a polymer bound anti-oxidant. The antioxidant can be present at a bound content level of between greater than 0 and 5% by weight, or between 0.1% and 1% or between 0.4% and 0.5%, or any combinations thereof.

One exemplary antioxidant is MADA, which is advantageously reacted with the rubber in the latex via a free radical addition reaction in which the sulfur group becomes bound to the rubber. The resulting rubber contains MADA that is chemically bound to the rubber backbone and resists extraction.

Although the present disclosure is directed partially to the use of MADA as the anti-oxidant, it is envisioned that a variety of other anti-oxidants capable of chemically bonding with the natural rubber prior to the resin extraction stage are viable options. For example, several amine and phenolic based anti-oxidants are believed to be viable for this undertaking. Specific reference is made to the article Polymer-Bound Antioxidants, vol. 57 Rubber Chemistry and Technology 621-651, J A Kuczkowski and J G Gillick for a teaching of suitable anti-oxidants. The disclosure of this article is herein incorporated by reference.

MADA can be produced according to the following process. Add 18.4 g of 4-aminodiphenylamine, 9.2 g of thioglycolic acid and 150 mL of xylene to a 500 ml. round bottom flask equipped with a Dean-Stark trap. Heat the flask under nitrogen to reflux (about 140° C.). Allow the reaction to proceed until the 1.8 mls of water are collected in the Dean-Stark trap. Allow the reaction mixture to cool to slightly above room temperature. Crude MADA is isolated by addition of hexane to the reaction mixture followed by recrystallizing the crude product from toluene. The MADA should be stored under nitrogen.

Examples

MADA was added to *Hevea* natural rubber latex (obtained from Lee Latex Limited, Singapore) and guayule rubber latex (obtained from Yulex Corporation, Maricopa, Ariz.). An example of the procedure for reacting MADA with latex is as follows: add 0.375 g of Galenol 2100 (a non-ionic surfactant available from Sasol Chemicals) to a 250 ml beaker followed by 121 mL of water. Heat and stir the contents until the Galenol dissolves in the water then cool to room temperature. Using a mortar and pestle, finely grind 2.63 g (0.01 mol) of MADA and transfer the material to the Galenol solution and stir the mixture vigorously until the MADA is homogeneously dispersed. Charge 129 g of latex containing 58% dry rubber content (DRC) to a 500 ml round bottom flask. Add the MADA dispersion to the latex and heat to 60° C. (140° F.) with gentle stirring for 8 hours under a nitrogen atmosphere. Coagulate the latex using a 5% acetic acid/1% calcium chloride solution and dry the rubber in a vacuum oven at 25 C until constant weight is reached. Extract the rubber in the continuous extraction unit described below to remove unreacted MADA and resins.

Figure 2:
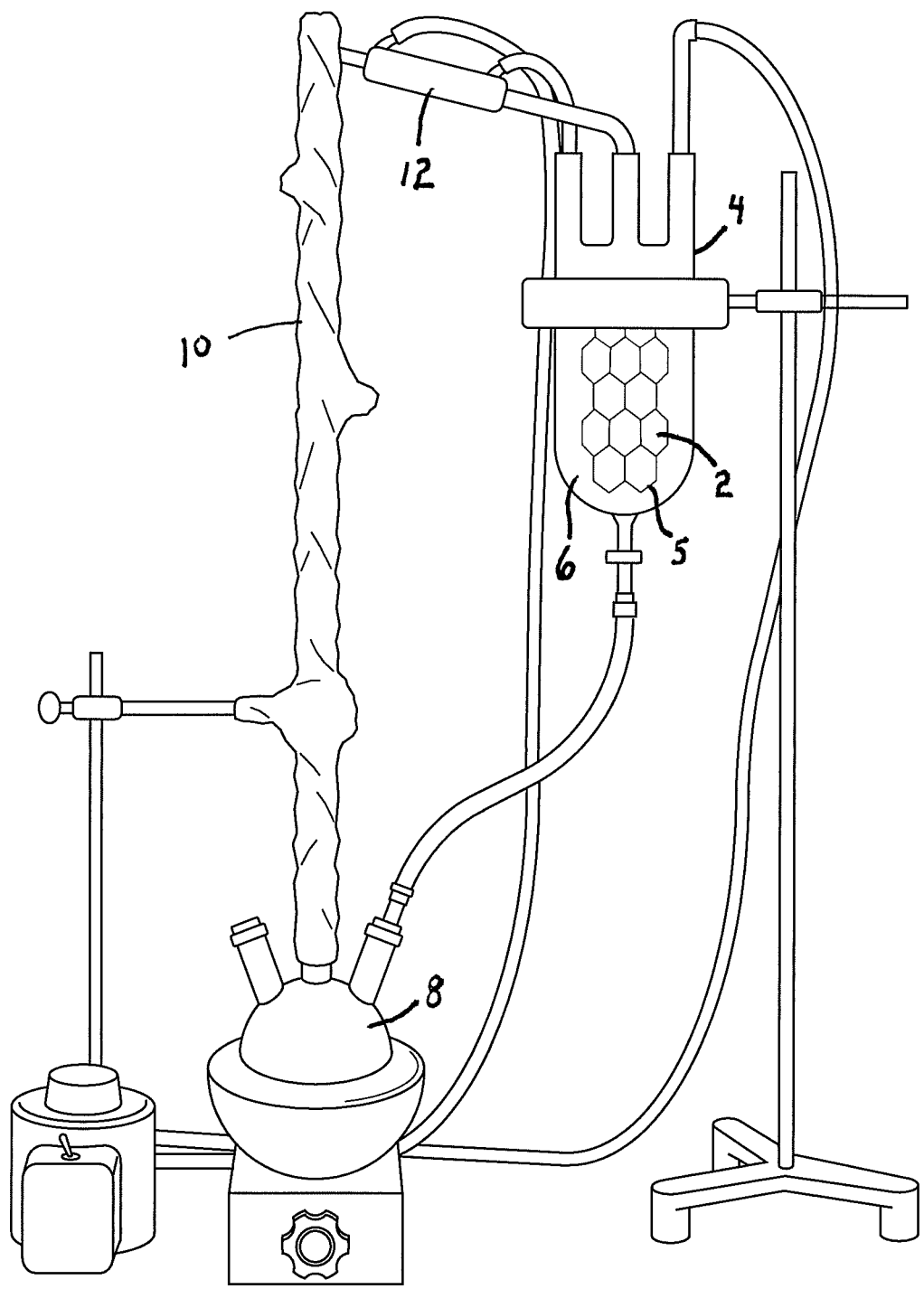
FIG. 2 illustrates a continuous extraction unit.

With reference to FIG. 2, a sheet of rubber 2 to be extracted is rolled up and placed in an extraction flask 4. As an example, the rubber sheet can have a gauge of less than 0.3 inches. Generally, the smaller the gauge the faster the extraction time. The sheet of rubber can be supported on a porous support 5, such as the chicken wire illustrated. The extraction flask is filled with extraction solvent 6 so that the rubber is completely submerged in the extraction solvent. Extraction solvent is also added to the boiling flask 8 to ensure a constant flow of solvent. The extraction flask is continuously drained and the resulting combination of extraction solvent and extract is fed to the boiling flask. Preferably, the column 10 connecting the boiling flask and the condenser 12 is insulated. The boiling flask is heated to vaporize the solvent, leaving the extract in the boiling flask. Preferably, the extraction flask will be equipped with a thermometer to assure that a proper reaction temperature is maintained. The solvent vapors are condensed in the condenser and the liquid solvent travels into the extraction flask, providing the extraction flask with a constant stream of fresh solvent.

For the control samples, natural rubber latex and guayule rubber latex were coagulated using the same 5% acetic acid/1% calcium chloride solution used to coagulate the latex reacted with MADA. The resulting rubber was extracted in the continuous extractor using acetone and dried in a vacuum oven set to 25° C. until a constant weight was achieved. The natural rubber samples were extracted for 8 hours at 25° C. and the guayule rubber samples were extracted for 16 hours at 35° C.

The extractable content of all samples was determined by Soxhlet extraction with acetone for 4 hours at 60° C. The samples were also tested for gel using a modified ASTM D3616 procedure and using the Mooney retention index test described earlier. The bound content of MADA was determined by pyrolysis gas chromatography/mass spectroscopy (GC/MS) as shown below.

To determine the amount of incorporated MADA as a total percentage of the polymer, control rubber was prepared which contained 0%, 0.75%, 1.5%, and 3.0% MADA, then analyzed via pyrolysis GC/MS. Results from these controls were compared to the rubber specimens that were reacted with MADA. To prepare the control specimens, 10 g of rubber was dissolved in 666.7 g of dichloromethane. The resulting mixture was separated into four separate flasks and the ground MADA was added in the amount of 0%, 0.75%, 1.5% and 3% by weight of rubber. The samples were stirred overnight and then poured into an aluminum pan and the solvent was allowed to evaporate. The resulting rubber was retrieved from the pan and submitted for pyrolysis GC/MS testing.

The primary means of determining a precise measurement of bound MADA in both natural rubber and guayule polymer systems was pyrolysis GC/MS of the solid rubber samples. The general pyrolysis GC/MS technique is described in Peter Kusch (2012). Pyrolysis-Gas Chromatography/Mass Spectrometry of Polymeric Materials, Advanced Gas Chromatography—Progress in Agricultural, Biomedical and Industrial Applications, Dr. Mustafa Ali Mohd (Ed.), ISBN: 978-953-51-0298-4 which is incorporated by reference. Detailed chromatography conditions for the analysis are shown in Table 3.

TABLE 3

| Conditions for GC/MS analysis of rubber containing MADA | |
|---|---|
| Injection temperature | 300° C. |
| Column/column length/film thickness | DB-5 ms/30 meter/ 0.25 micrometer |
| Split ratio | 20/1 |
| Pyrolysis temperature | 600° C. |
| Temperature program | Initial temperature 60° C. Increase temperature to 310° C. @ 25° C./min Hold for 230 minutes |
| Carrier flow | 24.7 ml/min |

To determine peaks of interest, an initial pyrolysis of pure MADA was performed. From examination of the gas chromatograph, two peaks of interest were those with retention times of 9.892 and 12.025 minutes. Both mass spectrographs of the peaks display strong similarities to the mass spectrograph of 1,4-Benzenediamine, N-phenyl, namely a major peak for a mass number of 184, which is a metabolite of MADA. The primary emphasis of this analysis was the initial 1,4-Benzenediamine, N-phenyl peak occurring around 9.9 minutes, the area of which was used to determine the MADA content for each control sample of the series for both natural rubber and guayule.

For each of the 0%, 0.75%, 1.5% and 3.0% MADA control samples of both natural rubber and guayule rubber, the sample was weighed and underwent pyrolysis GC/MS at 600° C. Manual peak integration was performed for the 1,4-Benzenediamine, N-phenyl peak at 9.9 minutes. The calculated result was divided by the sample weight, giving a normalized peak area. Subsequent plotting of the normalized peak area vs. the known percent MADA in the control samples produced a graph which could be used to determine MADA in the reacted/extracted samples. The result of implementing a linear trend line with the intercept set at the origin produces a linear equation with R squared values of 0.99 and 0.90 for the natural rubber and guayule rubber systems respectively.

Figure 3:
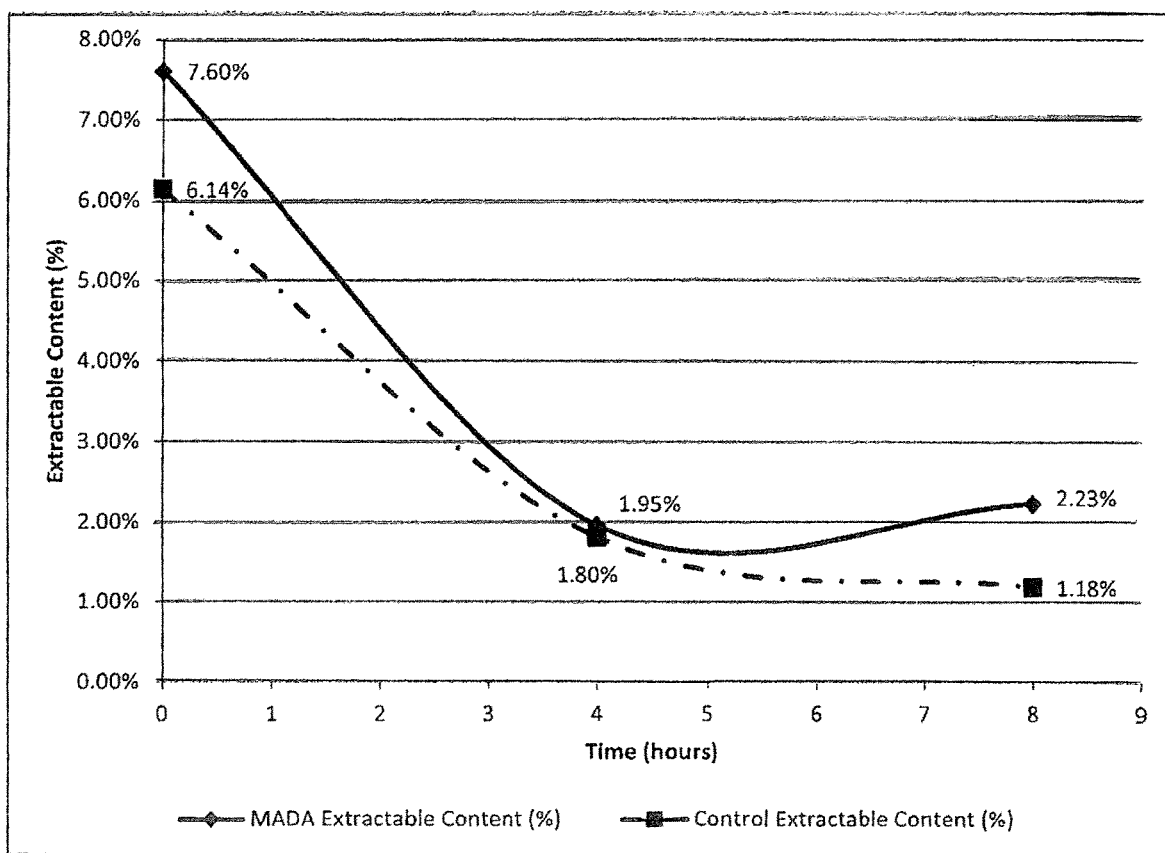
FIG. 3 depicts the extractable content for a natural rubber control and MADA incorporated samples as a function of extraction time.

ATR analysis confirmed the calculated results for each of the "MADA Incorporated" samples tested. The samples were compared at a wavenumber of 1514 for natural rubber and guayule rubber. The percent transmission (% T) for each sample was compared by plotting 100-% T as a function of the MADA percentage in the sample. This showed a linear relationship for both natural rubber and guayule rubber. The percentage MADA in the MADA incorporated samples was determined using the equation for the best fit line and the observed % T from the ATR results Reaction of MADA with Natural Rubber The extractable content data for the natural rubber control and MADA incorporated samples can be seen in Table 4. The extraction curves can be seen in FIG. 3. For natural rubber, the purpose of extracting the rubber is to remove the unbound MADA, therefore an extraction time of 8 hours is sufficient. The data shows that the extractable content leveled off after 8 hours of extraction which indicates that any unbound MADA present in the sample before extraction was removed during the extraction.

TABLE 4

Extractable content for Natural Rubber Samples

| Extraction Time (hours) | MADA Extractable Content (%) | Control Extractable Content (%) |
|---|---|---|
| 0 | 7.60% | 6.14% |
| 4 | 1.95% | 1.80% |
| 8 | 2.23% | 1.18% |

The gel content and MRI data for the natural rubber samples can be seen in Table 5. Because the gel content and Mooney viscosities of both the reacted and control samples are approximately the same, it indicates that the incorporation of MADA did not result in the crosslinking or breakdown of the rubber in the latex. After aging, however, there is a large drop in Mooney viscosity for the control sample which was not observed for the sample where MADA was incorporated. The aged sample degraded in the oven to the point of becoming a syrup because all of the natural antioxidants in the rubber were removed during the extraction step. On the contrary, the sample with bound MADA largely retained its original Mooney value, with an MRI of 89%, so it can be stated that MADA is an effective polymer bound antioxidant which provides stability to extraction media.

TABLE 5

Gel content and MRI data for natural rubber samples

| Property | Control | MADA Incorporated |
|---|---|---|
| Average Gel Content | 78.59% | 71.66% |
| Room Temperature Mooney | 72.62 | 65.94 |
| Aged Mooney | 1.83 | 58.94 |
| Mooney Retention Index | 2.52% | 89.38% |

Reaction of MADA with Guayule Rubber

Figure 4:
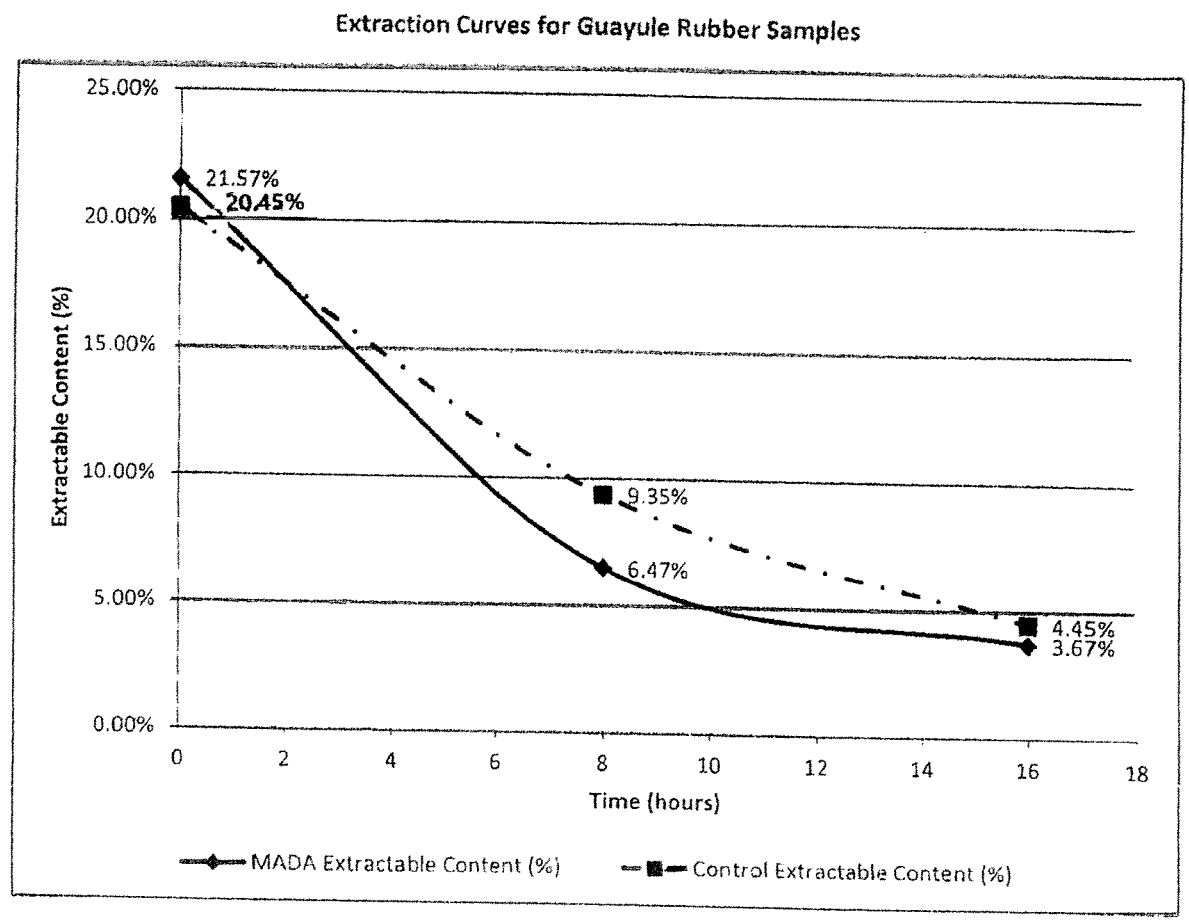
FIG. 4 depicts the extractable content for a guayule rubber control and MADA incorporated samples as a function of extraction time.

The extractable content data for the guayule rubber control and MADA incorporated samples can be seen in Table 6. The extraction curve can be seen in FIG. 4. The data shows that the initial extractable content of guayule was much higher than natural rubber (compare with natural rubber data in Table 4), but was significantly reduced during extraction.

TABLE 6

Extractable content for guayule rubber samples

| Extraction Time (hours) | MADA Extractable Content (%) | Control Extractable Content (%) |
|---|---|---|
| 0 | 21.57% | 20.45% |
| 8 | 6.47% | 9.35% |
| 16 | 3.67% | 4.45% |

The gel content and MRI data for the guayule rubber samples can be seen below in Table 7. The gel content of guayule rubber is typically around 5 or 6 percent. The gel content for the control is around 16%, indicating that the sample likely underwent some oxidation, which resulted in crosslinking of the rubber. However, for the sample with bound MADA, the gel content is 5.75%, indicating that the incorporation reaction did not gel the rubber. Similar to the natural rubber sample, there is a large difference in the aged Mooney viscosity and the room temperature Mooney viscosity for the guayule control sample. The aged sample degraded in the oven to the point of becoming a syrup because the antioxidants in the rubber were removed during the extraction step. Like the natural rubber sample with bound MADA, the guayule sample with bound MADA retained its original Mooney value, with an MRI of 104% (greater than 100% due to testing deviation limits).

TABLE 7

Gel content and MRI of guayule rubber samples

| Property | Control | MADA Incorporated |
|---|---|---|
| Average Gel Content | 16.39% | 5.75% |
| Room Temperature Mooney | 84.24 | 70.39 |
| Aged Mooney | 11.19 | 73.36 |
| Mooney Retention Index | 13.28% | 104.22% |

Bound Content Determination

The bound content for the MADA incorporated natural rubber sample and the MADA incorporated guayule rubber sample was calculated by GC pyrolysis to be 0.5 phr for both samples using the techniques discussed earlier. This result was deemed highly desirable because without being bound by theory, it is believed that a bound antioxidant content of between about 0.1 and 10.0% by weight, or between about 0.2 and 3.0% by weight, or between about 0.4 and 1.5% by weight is advantageous. Particularly, about 0.1% by weight is believed to provide a lower limit of effective oxidation resistance and by maintaining a content below about 10.0% by weight pro-oxidation can be avoided. An exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A method for stabilizing a guayule rubber comprising a first step of (i) combining a non-ionic surfactant with water to form a solution, (ii) homogeneously dispersing MADA in the solution, (iii) introducing the MADA inclusive solution to a latex form of the rubber, and (iv) heating such that the MADA becomes chemically bound to the rubber, a second step of coagulating the rubber, and a subsequent step of continuously treating said rubber to remove at least a substantial portion of entrained resins and achieve a rubber including less than 4% by weight resins.

2. The method of claim 1 wherein the guayule rubber contains greater than at least about 7% by weight entrained resins prior to extraction.

3. The method of claim 1 wherein said treating comprises contacting said rubber with a polar solvent.

4. The method of claim 3 wherein the polar solvent is acetone.

5. The method of claim 3 wherein the polar solvent is an alcohol containing four or fewer carbons.

6. The method of claim 3 wherein the polar solvent consists of a mixture of acetone and a hydrocarbon.

7. The method of claim 1 wherein said treated rubber includes less than 3% by weight resins.

8. A method for stabilizing a non-Hevea natural rubber comprising the step of introducing at least one of an amine and a phenolic anti-oxidant to a latex form of the rubber under conditions such that the anti-oxidant becomes chemically bound to the rubber and subsequently treating said rubber with an extraction solvent consisting of acetone to remove at least a substantial portion of entrained resins and achieve a rubber including less than 4% by weight resins and anti-oxidant between greater than 0 and 5% by weight.

9. A method of preparing guayule rubber comprising first forming a guayule latex, next introducing an antioxidant to said guayule rubber latex for a sufficient time to allow the antioxidant to become chemically bound to the guayule rubber, then coagulating the antioxidant inclusive guayule latex, and finally continuously extracting the coagulated rubber with a polar solvent, said continuously extracting comprising disposing the guayule rubber coagulated from the antioxidant inclusive guayule latex on a porous substrate and continuously introducing a recirculation of the polar solvent.

10. The method of claim 1 wherein the subsequent step of treating said rubber to remove at least a substantial portion of entrained resins is a continuous process using a heated extraction solvent for vapor removal of resins.

11. The method of claim 8 wherein the anti-oxidant is present between about 0.1 and 10.0% by weight.

12. The method of claim 8 wherein the anti-oxidant is present between about 0.2 and 3.0% by weight.

13. The method of claim 8 wherein the anti-oxidant is present between about 0.4 and 1.5% by weight.

14. The method of claim 13 wherein said rubber comprises guayule.

15. The method of claim 9 wherein the antioxidant is introduced to the guayule rubber latex in combination with a non-ionic surfactant.

16. The method of claim 15 wherein the non-ionic surfactant comprises ethoxolated alcohol.

17. The method of claim 10 wherein the coagulated rubber is placed in an extraction vessel and submerged in an extraction solvent for the subsequent step, said extraction solvent being separately heated before continuous introduction to the extraction vessel, wherein the extraction solvent carries extract in solvent vapors for collection.

* * * * *